(12) United States Patent
Nappa et al.

(10) Patent No.: US 7,795,482 B2
(45) Date of Patent: Sep. 14, 2010

(54) METHOD OF HYDRODECHLORINATION TO PRODUCE DIHYDROFLUORINATED OLEFINS

(75) Inventors: Mario Joseph Nappa, Newark, DE (US); Ekaterina N. Swearingen, Wilmington, DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 12/147,644

(22) Filed: Jun. 27, 2008

(65) Prior Publication Data
US 2009/0012335 A1    Jan. 8, 2009

Related U.S. Application Data

(60) Provisional application No. 60/958,190, filed on Jul. 3, 2007, provisional application No. 61/004,518, filed on Nov. 27, 2007.

(51) Int. Cl.
*C07C 17/10* (2006.01)
*C07C 21/18* (2006.01)
(52) U.S. Cl. .................. 570/176; 570/136
(58) Field of Classification Search .......... None
See application file for complete search history.

(56) References Cited

U.S. PATENT DOCUMENTS

| 2,774,799 | A | 12/1956 | Mantell et al. |
| 2,802,887 | A | 8/1957 | Miller et al. |
| 2,900,423 | A | 8/1959 | Smith |
| 5,068,472 | A | 11/1991 | Webster et al. |
| 5,118,888 | A | * 6/1992 | Gervasutti et al. .......... 570/153 |
| 5,243,103 | A | 9/1993 | Lerot et al. |
| 5,892,135 | A | 4/1999 | Manogue et al. |

FOREIGN PATENT DOCUMENTS

| EP | 0053657 | * | 6/1982 |
| EP | 0611745 | A1 | 8/1994 |
| GB | 974612 | | 11/1964 |
| JP | 05194286 | A | 8/1993 |
| JP | 05213793 | A | 8/1993 |
| WO | 9008748 | A1 | 8/1990 |
| WO | 9505353 | * | 2/1995 |
| WO | WO 95/05353 | A1 | 2/1995 |

OTHER PUBLICATIONS

Boudart et al., Journal of Catalysis, vol. 81, 1983, pp. 204-213.
Satterfield, Heterogeneous Catalysis in Industrial Practice, $2^{nd}$ Edition, Chapter, 4, McGraw-Hill, NY, 1991, pp. 87-112.
CRC Handbook of Chemistry and Physics, $81^{st}$ Edition, 2000-2001 (Book not included).
Chemical Abstract, "Synthesis Of Perfluoro-2-Butyne", Li, Zong-Zhen et. al., Jan. 1, 1981, XP-002573948.
PCT Search Report Application PCT/US09/069000, correspondent application to U.S. Appl. No. 12/641,875, Mar. 18, 2010.

* cited by examiner

*Primary Examiner*—Karl J Puttlitz

(57) ABSTRACT

Disclosed herein is a process for the preparation of fluorine-containing olefins comprising contacting a chlorofluoroalkene with hydrogen in the presence of a catalyst at a temperature sufficient to cause replacement of the chlorine substituents with hydrogen. Also disclosed is a catalyst composition for the hydrodechlorination of chlorofluoroalkenes comprising copper metal deposited on a support.

13 Claims, No Drawings

METHOD OF HYDRODECHLORINATION TO PRODUCE DIHYDROFLUORINATED OLEFINS

CROSS REFERENCE(S) TO RELATED APPLICATION(S)

This application claims the benefit of priority of U.S. Provisional Applications 60/958,190, filed Jul. 3, 2007, and 61/004,518, filed Nov. 27, 2007.

BACKGROUND INFORMATION

1. Field of the Disclosure

This disclosure relates in general to methods of synthesis of fluorinated olefins.

2. Description of the Related Art

The fluorocarbon industry has been working for the past few decades to find replacement refrigerants for the ozone depleting chlorofluorocarbons (CFCs) and hydrochlorofluorocarbons (HCFCs) being phased out as a result of the Montreal Protocol. The solution for many applications has been the commercialization of hydrofluorocarbon (HFC) compounds for use as refrigerants, solvents, fire extinguishing agents, blowing agents and propellants. These new compounds, such as HFC refrigerants, HFC-134a and HFC-125 being the most widely used at this time, have zero ozone depletion potential and thus are not affected by the current regulatory phase-out as a result of the Montreal Protocol.

In addition to ozone depleting concerns, global warming is another environmental concern in many of these applications. Thus, there is a need for compositions that meet both low ozone depletion standards as well as having low global warming potentials. Certain hydrofluoroolefins are believed to meet both goals. Thus there is a need for manufacturing processes that provide halogenated hydrocarbons and fluoroolefins that contain no chlorine that also have a low global warming potential.

SUMMARY

Disclosed is a process for the preparation of fluorine-containing olefins comprising contacting a chlorofluoroalkene with hydrogen in the presence of a catalyst at a temperature sufficient to cause replacement of the chlorine substituents of the chlorofluoroalkene with hydrogen to produce a fluorine-containing olefin. Also disclosed are catalyst compositions for the hydrodechlorination of chlorofluoroalkenes comprising copper metal deposited on a support, and comprising palladium deposited on calcium fluoride, poisoned with lead.

The foregoing general description and the following detailed description are exemplary and explanatory only and are not restrictive of the invention, as defined in the appended claims.

DETAILED DESCRIPTION

Disclosed is a process for the preparation of fluorine-containing olefins comprising contacting a chlorofluoroalkene with hydrogen in the presence of a catalyst at a temperature sufficient to cause replacement of the chlorine substituents of the chlorofluoroalkene with hydrogen to produce a fluorine-containing olefin. Also disclosed are catalyst compositions for the hydrodechlorination of chlorofluoroalkenes comprising copper metal deposited on a support, and comprising palladium deposited on calcium fluoride, poisoned with lead.

Many aspects and embodiments have been described above and are merely exemplary and not limiting. After reading this specification, skilled artisans appreciate that other aspects and embodiments are possible without departing from the scope of the invention. Other features and benefits of any one or more of the embodiments will be apparent from the following detailed description, and from the claims.

Before addressing details of embodiments described below, some terms are defined or clarified.

As used herein the term chlorofluoroalkene refers to compounds of the formula $R_fCCl{=}CClR_f$ wherein each $R_f$ is a perfluoroalkyl group independently selected from the group consisting of $CF_3$, $C_2F_5$, n-$C_3F_7$, i-$C_3F_7$, n-$C_4F_9$, i-$C_4F_9$ and t-$C_4F_9$, and wherein one of the $R_f$ groups may be F. As used herein, the chlorofluoroalkenes referred to may be either the E-stereoisomer, the Z-stereoisomer, or any mixture thereof.

As used herein, the term fluorine-containing olefin refers to compounds of formula E- or $Z{-}R^1CH{=}CHR^2$, wherein each of $R^1$ and $R^2$ are, perfluoroalkyl groups independently selected from the group consisting of $CF_3$, $C_2F_5$, n-$C_3F_7$, i-$C_3F_7$, n-$C_4F_9$, i-$C_4F_9$ and t-$C_4F_9$, and wherein $R^2$ may be F.

As used herein, an alloy is a metal that is a combination of two or more elements, at least one of which is a metal.

In one embodiment, the process is run in the presence of a catalyst.

Hydrogenation catalysts containing copper, nickel, chromium, palladium, and ruthenium are known in the art. They may be prepared by either precipitation methods or impregnation methods as generally described by Satterfield on pages 87-112 in *Heterogeneous Catalysis in Industrial Practice, 2$^{nd}$* edition (McGraw-Hill, New York, 1991).

In one embodiment, the catalyst for the process is selected from the group consisting of copper on carbon, copper on calcium fluoride, palladium on barium sulfate, palladium/barium chloride on alumina, Lindlar catalyst (palladium on $CaCO_3$, poisoned with lead), palladium on calcium fluoride poisoned with lead, copper and nickel on carbon, nickel on carbon, nickel on calcium fluoride, copper/nickel/chromium on calcium fluoride and unsupported alloys of copper and nickel.

In another embodiment, the catalyst is selected from the group consisting of copper on carbon, copper on calcium fluoride, copper and nickel on carbon, nickel on carbon, copper/nickel/chromium on calcium fluoride and unsupported alloys of copper and nickel. In one embodiment, the amount of copper on carbon or calcium fluoride support is from about 1% by weight to about 25% by weight. The carbon support may be acid washed carbon.

In one embodiment, the palladium on barium sulfate catalyst may contain from about 0.05% to 10% by weight palladium. In one embodiment, copper and nickel on carbon may contain from about 1% to about 25% by weight copper and nickel combined on the carbon support. The carbon support may be any of the carbon supports as described previously herein for other catalysts. The weight ratio of the copper to nickel in the copper and nickel on carbon catalyst may range from about 2:1 to about 1:2.

In one embodiment, the palladium/barium chloride on alumina catalyst may contain from about 1% to about 25% by weight barium chloride and from about 0.05% to about 10% by weight palladium relative to the total weight of the catalyst composition. Preparation of a palladium/barium chloride on alumina catalyst is described in U.S. Pat. No. 5,243,103, the disclosure of which is herein incorporated by reference.

In one embodiment, the palladium on calcium fluoride catalyst poisoned with lead may contain from about 0.02% to about 5% palladium by weight. In one embodiment, in the preparation of the palladium on calcium fluoride poisoned with lead catalyst, the ratio of lead acetate in solution to palladium on support is from about 0.5:1 to about 2:1.

In one embodiment, the molar ratio of copper:nickel:chromium oxide in the copper/nickel/chromium on calcium fluoride catalyst is from about 0 to about 1 copper, from about 0.5 to about 3.0 nickel, and from about 0 to about 2 chromium. In one embodiment, the molar ratio of copper:nickel:chromium in the copper/nickel/chromium on calcium fluoride catalyst is 1.0:1.0:1.0. In another embodiment, the molar ratio is 1.0:2.0:1.0. In yet another embodiment, the molar ratio is 1.0:2.0:0.25. In yet another embodiment, the molar ratio is 0.5:3.0:0.5. In yet another embodiment, the molar ratio is 0.5:0.5:2.0. In yet another embodiment, the molar ratio is 0:3.0:1.0. In yet another embodiment, the molar ratio is 1:3.0:0. In one embodiment, the weight ratio of total catalyst material to support material may be from about 1:2 to about 2:1. A method of preparation of the copper/nickel/chrome catalyst is described in U.S. Pat. No. 2,900,423, the disclosure of which is herein incorporated by reference.

In one embodiment, the unsupported alloys of copper and nickel include those described by Boudart in *Journal of Catalysis*, 81, 204-13, 1983, the disclosure of which is herein incorporated by reference. In one embodiment, the mole ratio of Cu:Ni in the catalysts may range from about 1:99 to about 99:1. In another embodiment, the mole ratio of Cu:Ni is about 1:1.

In one embodiment, the contact time for the process ranges from about 2 to about 120 seconds.

In one embodiment, the ratio of hydrogen to chlorofluoroalkene is from about 1:1 to about 7.5:1. In another embodiment, the ratio of hydrogen to chlorofluoroalkene is from about 1:1 to about 5:1. In another embodiment, the ratio of hydrogen to chlorofluoroalkene is from about 5:1 to about 10:1.

In one embodiment, the process for preparation of fluorine-containing olefins comprises reacting a chlorofluoroalkene with hydrogen in a reaction vessel constructed of an acid resistant alloy material. Such acid resistant alloy materials include stainless steels, high nickel alloys, such as Monel, Hastelloy, and Inconel. In one embodiment, the reaction takes place in the vapor phase.

In one embodiment, the temperature at which the process is run may be a temperature sufficient to cause replacement of the chlorine substituents with hydrogen. In another embodiment, the process is conducted at a temperature of from about 100° C. to about 450° C.

In some embodiments, the pressure for the hydrodechlorination reaction is not critical. In other embodiments, the process is performed at atmospheric or autogenous pressure. Means may be provided for the venting of the excess pressure of hydrogen chloride formed in the reaction and may offer an advantage in minimizing the formation of side products.

Additional products of the reaction may include partially hydrodechlorinated intermediates; saturated hydrogenated compounds; various partially chlorinated intermediates or saturated compounds; and hydrogen chloride (HCl). For example, wherein the chlorofluoroalkene is 2,3-dichloro-1,1,1,4,4,4-hexafluoro-2-butene (CFC-1316mxx, E- and/or Z-isomers), the compounds formed in addition to E- and/or Z-1,1,1,4,4,4-hexafluoro-2-butene (E- and/or Z-HFC-1336mzz) may include, 1,1,1,4,4,4-hexafluorobutane (HFC-356mff), pentafluorobutane (HFC-1345, different isomers), 2-chloro-1,1,1,1,4,4,4-hexafluorobutane (HFC-346mdf), E and/or Z-2-chloro-1,1,1,4,4,4-hexafluoro-2-butene (E- and/or Z-HCFC-1326mxz), and 1,1,1,4,4,4-hexafluoro-2-butyne (HFB).

In certain embodiments, the present disclosure provides a catalyst composition for the hydrodechlorination of chlorofluoroalkenes comprising copper metal deposited on a support.

In one embodiment, the catalyst composition for the hydrodechlorination of chlorofluoroalkenes comprises copper metal deposited on a support comprising acid-washed carbon or calcium fluoride.

In one embodiment, the catalyst composition for the hydrodechlorination of chlorofluoroalkenes comprises copper metal deposited on a support wherein said copper metal comprises about 5% to about 25% by weight of the catalyst composition.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

EXAMPLES

The concepts described herein will be further described in the following examples, which do not limit the scope of the invention described in the claims.

In the examples the follow abbreviations or codes may be used:

CT=contact time t-1336=E-1336mzz=E-$CF_3CH=CHCF_3$ c-1336=Z-1336mzz=Z—$CF_3CH=CHCF_3$ 356mff=$CF_3CH_2CH_2CF_3$

1345=$C_4H_3F_5$ 346 mdf=$CF_3CHClCH_2CF_3$

1326=E- and/or Z—$CF_3CH=CClCF_3$ t-1326mxz=Z-1326mxz=Z—$CF_3CH=CClCF_3$ c-1326mxz=E-1326 mxz=E-$CF_3CH=CClCF_3$ 1316mxx=E/Z—$CF_3CCl=CClCF_3$ t-1316mxx=E-1316mxx=E-$CF_3CCl=CClCF_3$ c-1316mxx=Z-1316mxx=Z—$CF_3CCl=CClCF_3$ 171-14mccxx=E/Z—$CF_3CF_2CF_2CCl=CClCF_2CF_2CF_3$ 173-14mcczz=E/Z—$CF_3CF_2CF_2CH=CHCF_2CF_2CF_3$ t-172-14=E-$CF_3CF_2CF_2CCl=CHCF_2CF_2CF_3$ c-172-14=Z—$CF_3CF_2CF_2CCl=CHCF_2CF_2CF_3$

HFB=$CF_3C≡CCF_3$

Example 1

Example 1 demonstrates the conversion of CFC-1316mxx to HFC-1336mzz over Cu on carbon catalyst.

An Inconel® tube (⅝ inch OD) was filled with 13 cc (5.3 gm) of 25% Cu on acid washed carbon (18-30 mesh). The temperature of the reactor was raised to 100° C. for 30 minutes under $N_2$ flow (30 sccm, $5.0×10^{-7}$ m³/sec). The temperature was then increased to 250° C. under $H_2$ flow for one hour. The temperature and flows were changed as described in the experiments in Table 1, below, and the reactor effluent was analyzed by GCMS to provide the following molar percent of products.

TABLE 1

| Temp ° C. | CT (sec) | Molar ratio $H_2$/1316 | Reactor effluent concentration (molar %) | | | | | |
|---|---|---|---|---|---|---|---|---|
| | | | t-1336 | 356mff | 1345 | c-1336 | 346mdf | 1316mxx | 1326 |
| 310 | 74 | 5.2:1 | 12 | 0 | 0 | 5 | 0 | 0 | 81 |
| 310 | 120 | 2.9:1 | 40 | 3 | 4 | 9 | 2 | 0 | 42 |
| 310 | 120 | 3.0:1 | 40 | 4 | 4 | 9 | 2 | 0 | 40 |
| 310 | 121 | 2.9:1 | 36 | 2 | 2 | 8 | 2 | 0 | 50 |
| 311 | 125 | 2.7:1 | 28 | 0 | 0 | 6 | 0 | 0 | 65 |
| 339 | 74 | 5.1:1 | 36 | 2 | 2 | 10 | 2 | 0 | 47 |
| 340 | 97 | 3.4:1 | 48 | 3 | 5 | 12 | 0 | 0 | 33 |
| 340 | 100 | 3.4:1 | 46 | 3 | 3 | 11 | 2 | 0 | 36 |
| 340 | 68 | 5.3:1 | 40 | 2 | 4 | 12 | 2 | 0 | 40 |
| 340 | 73 | 4.8:1 | 29 | 1 | 2 | 11 | 0 | 0 | 57 |
| 340 | 123 | 2.4:1 | 52 | 3 | 3 | 11 | 0 | 0 | 30 |
| 340 | 71 | 5.4:1 | 39 | 2 | 4 | 11 | 2 | 0 | 42 |
| 340 | 118 | 2.6:1 | 52 | 3 | 5 | 11 | 0 | 0 | 27 |

Example 2

Example 2 demonstrates the conversion of CFC-1316mxx to HFC-1336mzz over Pd/BaCl$_2$/Al$_2$O$_3$ catalyst.

A Hastelloy reactor 10"L×½" o.d.×0.034" wall was filled with 11 cc of the catalyst. The catalyst was conditioned at 150° C. for 65 hrs in hydrogen flow of 50 sccm (8.3×10$^{-7}$ m$^3$/sec). Then the temperature was raised to 300° C. for 2 hrs at the same flow. The hydrodechlorination of 1316mxx was studied at temperatures of 240-400° C. as indicated in Table 2. Products of the reaction were analyzed by GCMS to give the following molar concentrations.

TABLE 2

| Temp deg C. | CT (sec) | Molar ratio H$_2$/ 1316mxx | Reactor effluent concentration (molar %) | | | | | | | |
|---|---|---|---|---|---|---|---|---|---|---|
| | | | t-1336 | 1345 | 356mff | c-1336 | t-1326mxz | c-1326mxz | t-1316mxx | c-1316mxx |
| 240 | 30 | 1:1 | 11.96 | 0.65 | 7.58 | 1.14 | 19.41 | 0.62 | 49.70 | 1.82 |
| 240 | 30 | 1:1 | 11.39 | 0.57 | 7.81 | 1.13 | 20.35 | 0.64 | 49.21 | 1.79 |
| 300 | 10 | 2:1 | 23.55 | 3.38 | 13.30 | 1.39 | 27.14 | 0.27 | 15.98 | 0.26 |
| 300 | 10 | 2:1 | 22.31 | 2.55 | 14.59 | 1.35 | 27.50 | 0.32 | 17.76 | 0.37 |
| 325 | 30 | 1:1 | 26.95 | 0.30 | 3.14 | 3.80 | 19.77 | 0.99 | 38.91 | 3.06 |
| 325 | 30 | 1:1 | 24.08 | 0.30 | 2.63 | 4.92 | 18.51 | 1.00 | 42.39 | 3.31 |
| 350 | 30 | 1:1 | 23.51 | 1.72 | 6.66 | 7.15 | 22.53 | 0.80 | 29.95 | 2.17 |
| 400 | 30 | 1:1 | 17.66 | 1.43 | 2.40 | 1.19 | 15.65 | 1.01 | 47.46 | 7.84 |

Example 3

Example 3 demonstrates the conversion of CFC-1316mxx to HFC-1336mzz over Pd/BaSO$_4$ catalyst.

A Hastelloy reactor 10"L×½" o.d.×0.034" wall was filled with 11 cc (19.36 g) of the catalyst. The catalyst was conditioned at 300° C. for 2 hrs in hydrogen flow of 50 sccm (8.3×10$^{-7}$ m$^3$/sec). The hydrodechlorination of 1316mxx was studied at 100-200° C. as indicated in Table 3, below. The mole ratio of hydrogen to 1316mxx was 1:1. Contact time for all runs in Table 3 was 60 seconds. Products of the reaction were analyzed by GCMS to give the following molar concentrations.

TABLE 3

| Temp ° C. | Reactor effluent concentration (molar %) | | | | | | | |
|---|---|---|---|---|---|---|---|---|
| | t-1336 | 356mff | c-1336 | t-1326mxz | 346mdf | c-1326mxz | t-1316mxx | c-1316mxx |
| 200 | 10.64 | 13.35 | 0.45 | 31.66 | 10.91 | 0.90 | 29.81 | 0.54 |
| 200 | 10.25 | 13.40 | 0.44 | 30.56 | 10.16 | 0.99 | 31.85 | 0.61 |

Example 4

Example 4 demonstrates the conversion of CFC-1316mxx to HFC-1336mzz over Lindlar catalyst.

Lindlar catalyst (from Strem Chemicals, Inc., Newburyport, Mass., USA) was pelletized and sieved to 12/20 mesh. 25 g of the catalyst was loaded into a Hastelloy reactor 10"L×½" o.d.×0.034" wall thickness. The catalyst was conditioned at 300° C. for 2 hrs in hydrogen flow of 50 sccm ($8.3 \times 10^{-7}$ m$^3$/sec). The hydrodechlorination of 1316mxx was studied at 200-250° C. The mole ratio of hydrogen:1316 was 2:1 and the contact time was 45 seconds for all runs in Table 4. Products of the reaction were analyzed by GCMS to give the following molar concentrations.

TABLE 4

| Temp | Reactor effluent concentration (molar %) | | | | | | | |
|---|---|---|---|---|---|---|---|---|
| ° C. | t-1336 | 356mff | c-1336 | t-1326mxz | 346mdf | c-1326mxz | t-1316mxx | c-1316mxx |
| 200 | 6.17 | 7.64 | 19.74 | 25.59 | 0.28 | 0.29 | 38.00 | 1.20 |
| 200 | 3.39 | 4.04 | 14.07 | 20.34 | 0.29 | 0.53 | 53.90 | 2.31 |
| 250 | 2.33 | 1.03 | 49.75 | 7.70 | 0.00 | 0.66 | 33.03 | 2.82 |

Example 5

Example 5 demonstrates the conversion of CFC-1316mxx to HFC-1336mzz over Cu on carbon catalyst.

In a 400 ml Pyrex beaker a solution of 10.73 g CuCl$_2$.2H$_2$O was prepared in 65 ml of 10% HCl in deionized water. 46.0 g of acid washed carbon (10/30 mesh) was added to the solution. The stiff slurry was allowed to stand at room temperature for 1 hr with occasional stirring. Then the slurry was dried at 110-120° C. under air overnight. After that the catalyst was transferred into quartz tube which was purged with 500 sccm ($8.3 \times 10^{-6}$ m$^3$/sec) N$_2$ at 25° C. for 15 min, then 100 sccm each He and H$_2$ for 15 min. Then the catalyst was heated at 5° C./min to 500° C. for 6 hrs in He/H$_2$. The procedure gave 48.52 g of catalyst.

A Hastelloy reactor 10"L×½" o.d.×0.034" wall was filled with 11 cc (4.73 g) of 8% Cu on acid washed carbon catalyst. The catalyst was conditioned at 150° C. for 16 hrs in hydrogen flow of 50 sccm ($8.3 \times 10^{-7}$ m$^3$/sec). The temperature was raised to 350° C. for 2 hrs in hydrogen flow of 50 sccm ($8.3 \times 10^{-7}$ m$^3$/sec). The hydrodechlorination of 1316mxx was studied at temperatures ranging from about 300 to 400° C. as indicated in Table 5, below. Products of the reaction were analyzed by GCMS to give the following molar concentrations.

TABLE 5

| | | | Reactor effluent concentration (molar %) | | | | | | | |
|---|---|---|---|---|---|---|---|---|---|---|
| Temp ° C. | CT (sec) | Molar ratio H$_2$/1316 | t-1336 | 1345 | 356mff | c-1336 | t-1326mxz | c-1326mxz | t-1316mxx | t-1316mxx |
| 300 | 30 | 4:1 | 0.58 | 0.0 | 0.40 | 0.09 | 31.47 | 1.65 | 34.41 | 29.85 |
| 300 | 60 | 4:1 | 1.65 | 0.0 | 1.18 | 0.12 | 73.93 | 4.16 | 5.16 | 11.72 |
| 340 | 60 | 4:1 | 27.34 | 0.06 | 0.90 | 1.38 | 66.35 | 2.87 | 0.0 | 0.0 |
| 340 | 75 | 5:1 | 56.81 | 1.18 | 3.42 | 3.25 | 32.00 | 1.14 | 0.0 | 0.0 |
| 325 | 75 | 5:1 | 35.80 | 0.66 | 2.62 | 2.63 | 53.64 | 2.05 | 0.0 | 0.0 |
| 360 | 75 | 5:1 | 68.83 | 2.54 | 5.14 | 3.21 | 17.76 | 0.63 | 0.0 | 0.0 |
| 360 | 75 | 5:1 | 66.08 | 2.63 | 5.27 | 3.39 | 19.91 | 0.68 | 0.0 | 0.0 |
| 400 | 75 | 5:1 | 65.00 | 9.13 | 17.40 | 2.10 | 0.48 | 0.00 | 0.0 | 0.0 |
| 400 | 50 | 5:1 | 69.78 | 5.93 | 8.94 | 4.39 | 7.07 | 0.08 | 0.0 | 0.0 |

Example 6

Example 6 demonstrates the conversion of CFC-1316mxx to HFC-1336mzz over Cu on calcium fluoride catalyst.

A Hastelloy reactor 10"L×½" o.d.×0.034" wall was filled with 10.5 cc (15.22 g) of 8% Cu on $CaF_2$ catalyst. The catalyst was conditioned at 300° C. for 18 hrs in hydrogen flow of 50 sccm ($8.3 \times 10^{-7}$ m³/sec). The hydrodechlorination of 1316mxx was studied at a temperature range of 250-450° C. as indicated in Table 6, below. The contact time was 45 seconds and the mole ratio of hydrogen:1316 was 5:1 for all runs in Table 6. Products of the reaction were analyzed by GCMS to give the following molar concentrations.

TABLE 6

| Temp | Reactor effluent concentration (molar %) | | | | | | | |
|---|---|---|---|---|---|---|---|---|
| ° C. | HFB | t-1336 | 356mff | c-1336 | t-1326mxz | c-1326mxz | t-1316mxx | c-1316mxx |
| 250 | 0.32 | 0.21 | 0.43 | 0.68 | 0.72 | 0.12 | 87.73 | 9.21 |
| 250 | 0.27 | 0.21 | 0.38 | 0.59 | 0.71 | 0.12 | 87.65 | 9.49 |
| 300 | 0.86 | 0.14 | 0.24 | 0.28 | 0.92 | 0.19 | 87.01 | 9.66 |
| 300 | 0.95 | 0.16 | 0.31 | 0.15 | 1.04 | 0.21 | 87.14 | 9.48 |
| 400 | 8.04 | 0.16 | 0.22 | 0.11 | 1.77 | 0.42 | 75.64 | 12.98 |
| 450 | 3.36 | 0.13 | 0.19 | 0.09 | 1.93 | 0.48 | 58.16 | 35.07 |

Example 7

Example 7 demonstrates the conversion of CFC-1316mxx to HFC-1336 over Cu/Ni on carbon catalyst.

A Hastelloy reactor 15"L×1" o.d.×0.074" wall was filled with 23 cc (8.7 g) of 1% Cu/1% Ni on carbon catalyst. The catalyst was conditioned with 50 sccm ($8.3 \times 10^{-7}$ m³/sec) of hydrogen flow according to the following protocol: 1 hr at 50° C., followed by 1 hr at 100° C., followed by 1 hr at 150° C., followed by 1 hr at 200° C., followed by 1 hr at 250° C., followed by 2 hr at 300° C., followed by a final 16 hrs at 200° C.

The hydrodechlorination of 1316mxx was studied over a temperature range of 200-375° C. Products of the reaction were analyzed by GCMS to give the molar concentrations as listed in Table 7.

TABLE 7

| Temp | CT | Molar ratio | Reactor effluent concentration (molar %) | | | | | |
|---|---|---|---|---|---|---|---|---|
| ° C. | (sec) | $H_2$/1316 | t-1336 | c-1336 | t-1326mxz | c-1326mxz | t-1316mxx | c-1316mxx |
| 200 | 75 | 5:1 | 0.14 | 0.47 | 40.50 | 1.24 | 51.34 | 5.38 |
| 300 | 75 | 5:1 | 7.10 | 0.61 | 87.28 | 3.91 | 0.08 | 0.12 |
| 300 | 75 | 7.5:1 | 34.31 | 4.04 | 58.68 | 1.64 | 0.00 | 0.00 |
| 350 | 30 | 7.5:1 | 60.33 | 6.51 | 29.96 | 0.47 | 0.00 | 0.00 |
| 375 | 30 | 7.5:1 | 75.71 | 6.98 | 8.41 | 0.05 | 0.00 | 0.00 |

Example 8

Example 8 demonstrates the conversion of CFC-1316mxx to HFC-1336mzz over Ni on carbon catalyst.

A Hastelloy reactor 15"L×1" o.d.×0.074" wall was filled with 23 cc (10.58 g) of 8% Ni on carbon catalyst. The catalyst was conditioned at 50 sccm ($8.3\times10^{-7}$ m$^3$/sec) of hydrogen flow according to the following protocol: 1 hr at 50° C., followed by 1 hr at 100° C., followed by 1 hr at 150° C., followed by 1 hr at 200° C., followed by 1 hr at 250° C., followed by 2 hrs at 300° C., and finally followed by 16 hrs at 250° C.

The hydrodechlorination of 1316mxx was studied at a temperature range of 250-375° C. Products of the reaction were analyzed by GCMS to give the molar concentrations as listed in Table 8.

TABLE 8

| Temp ° C. | CT (sec) | Molar ratio H$_2$/1316 | HFB | t-1336 | 1345 | 356mff | c-1336 | t-1326mxz | c-1326mxz | t-1316mxx | c-1316mxx |
|---|---|---|---|---|---|---|---|---|---|---|---|
| 250 | 30 | 7.5:1 | 0.00 | 0.30 | 0.0 | 0.08 | 1.53 | 12.01 | 0.65 | 73.11 | 11.75 |
| 275 | 30 | 7.5:1 | 0.04 | 0.51 | 0.04 | 0.12 | 3.13 | 17.14 | 0.90 | 54.74 | 22.59 |
| 300 | 30 | 7.5:1 | 0.13 | 1.24 | 0.08 | 0.19 | 5.65 | 27.44 | 1.32 | 36.19 | 26.62 |
| 325 | 30 | 7.5:1 | 0.39 | 3.71 | 0.15 | 0.28 | 8.84 | 44.78 | 2.13 | 20.05 | 18.01 |
| 350 | 30 | 7.5:1 | 1.04 | 12.05 | 0.30 | 0.48 | 11.69 | 58.59 | 2.68 | 5.70 | 5.12 |
| 375 | 30 | 7.5:1 | 0.74 | 30.63 | 0.62 | 1.12 | 11.84 | 47.46 | 1.78 | 1.00 | 0.86 |
| 375 | 75 | 7.5:1 | 0.04 | 61.30 | 1.29 | 3.06 | 6.97 | 21.86 | 0.39 | 0.00 | 0.00 |
| 375 | 75 | 4:1 | 0.19 | 49.61 | 0.59 | 1.17 | 8.05 | 34.63 | 1.02 | 0.13 | 0.12 |

Example 9

Example 9 demonstrates the conversion of CFC-1316mxx to HFC-1336mzz over Ni on calcium fluoride catalyst.

In a 400 ml Pyrex beaker a solution of 5.698 g Ni(NO$_3$)$_2$.6H$_2$O was prepared in 25 ml of deionized water. 21.76 g of CaF$_2$ (12/30 mesh, sintered) was added to the solution. 46.0 g of acid washed carbon (10/30 mesh) was added to the solution. The mixture was placed on a warm hotplate and dried to a damp solid 150-160° C. under air overnight. Then the catalyst was placed in quartz tube which was purged with 500 sccm ($8.3\times10^{-6}$ m$^3$/sec) N$_2$ at 25° C. for 30 min, then 100 sccm each of He and H$_2$ for 15 min. Then the catalyst was heated at 0.5° C./min to 350° C. for 12 hrs in He/H$_2$. After cooling in He/H$_2$, the sample was passivated in 2% O$_2$.N$_2$ at room temperature for 30 min. 22.728 g of the catalyst was made.

A Hastelloy reactor 15"L×1" o.d.×0.074" wall was filled with 23 cc (15.24 g) of 5% Ni on CaF$_2$ catalyst. The catalyst was conditioned at 50 sccm ($8.3\times10^{-7}$ m$^3$/sec) hydrogen Flow according to the following protocol: 1 hr at 50° C., followed by 1 hr at 100° C., followed by 1 hr at 150° C., followed by 1 hr at 200° C., and finally followed by 16 hr at 250° C.

The hydrodechlorination of 1316mxx was studied at a temperature range of 250-450° C. and the products indicated in Table 9, below. Contact time was 75 seconds in all cases. The ratio of hydrogen to 1316mxx was 5:1 in all cases. Products of the reaction were analyzed by GCMS to give the molar concentrations as listed in Table 9.

TABLE 9

| Temp ° C. | t-1336 | 1345 | 356mff | c-1336 | t-1326mxz | c-1326mxz | t-1316mxx | c-1316mxx |
|---|---|---|---|---|---|---|---|---|
| 250 | 0.09 | 0.23 | 0.64 | 2.45 | 1.08 | 0.19 | 84.59 | 9.49 |
| 400 | 7.52 | 1.42 | 1.93 | 29.96 | 3.37 | 0.54 | 31.20 | 13.76 |

TABLE 9-continued

| Temp | Reactor effluent concentration (molar %) | | | | | | | |
|---|---|---|---|---|---|---|---|---|
| °C. | t-1336 | 1345 | 356mff | c-1336 | t-1326mxz | c-1326mxz | t-1316mxx | c-1316mxx |
| 450 | 12.37 | 1.40 | 3.54 | 35.69 | 3.07 | 0.41 | 14.26 | 12.00 |
| 450 | 2.49 | 0.34 | 0.81 | 12.95 | 1.97 | 0.40 | 39.60 | 33.21 |

Example 10

Example 10 demonstrates the conversion of CFC-1316mxx to HFC-1336mzz over a Cu/Ni/Cr on calcium fluoride catalyst.

A Hastelloy reactor 10"L×½" o.d.×0.034" wall was filled with 11 cc of Cu/Ni/Cr/CaF2 (with molar ratio of metals 1:1:1) catalyst made by the process described in U.S. Pat. No. 2,900,423. This catalyst was analyzed by X-Ray Fluorescence and found to contain (mole %) 61.0% F, 13.5% Ca, 9.4% Cr, 6.9% Ni, and 6.1% Cu, and 3.0% K. The catalyst was conditioned at 250° C. for 90 hrs in hydrogen flow of 50 sccm ($8.3 \times 10^{-7}$ m$^3$/sec). The temperature was raised to 400° C. for 2 hrs in hydrogen flow of 50 sccm ($8.3 \times 10^{-7}$ m$^3$/sec). The hydrodechlorination of 1316mxx was studied at a temperature range of 350-450° C., as indicated by the results in Table 10, below. For all runs in Table 10, the ratio of hydrogen:1316 was 2:1. Products of the reaction were analyzed by GCMS to give the molar concentrations as listed in table 10.

TABLE 10

| Temp | CT | Reactor effluent concentration (molar %) | | | | | | | |
|---|---|---|---|---|---|---|---|---|---|
| °C. | (sec) | HFB | t-1336 | 356mff | c-1336 | t-1326mxz | c-1326mxz | t-1316mxx | c-1316mxx |
| 350 | 15 | 22.9 | 0.4 | 0.0 | 1.8 | 3.7 | 0.3 | 61.9 | 6.7 |
| 400 | 15 | 29.5 | 0.7 | 0.0 | 3.2 | 2.8 | 0.3 | 53.4 | 6.8 |
| 450 | 15 | 30.5 | 0.6 | 0.4 | 0.8 | 2.2 | 0.4 | 41.2 | 14.8 |
| 400 | 30 | 40.5 | 0.9 | 0.7 | 2.3 | 5.0 | 0.6 | 35.1 | 6.8 |
| 400 | 45 | 43.3 | 1.1 | 0.6 | 2.7 | 6.0 | 0.7 | 30.1 | 6.1 |
| 450 | 45 | 53.1 | 4.5 | 0.4 | 10.7 | 6.1 | 0.5 | 8.5 | 3.9 |

Example 11

Example 11 demonstrates the conversion of CFC-1316mxx to HFC-1336mzz over a Cu/Ni/Cr on calcium fluoride catalyst.

A Hastelloy reactor 10"L×½" o.d.×0.034" wall was filled with 11 cc of Cu/Ni/Cr/CaF2 (with molar ratio of metals 1:2:1) catalyst made by the process described in U.S. Pat. No. 2,900,423. The catalyst was conditioned at 400° C. for 2 hrs in hydrogen flow of 50 sccm ($8.3 \times 10^{-7}$ m$^3$/sec). The hydrodechlorination of 1316mxx was studied at a temperature range of 350-450° C. Products of the reaction were analyzed by GCMS to give the molar concentrations as indicated by the results in Table 11, below.

TABLE 11

| Temp | CT | Molar Ratio | Reactor effluent concentration (molar %) | | | | | | | |
|---|---|---|---|---|---|---|---|---|---|---|
| °C. | (sec) | H$_2$/1316 | HFB | t-1336 | c-1336 | 1345 | t-1326mxz | c-1326mxz | t-1316mxx | c-1316mxx |
| 350 | 30 | 2:1 | 16.91 | 2.77 | 22.22 | 6.90 | 16.96 | 2.25 | 19.55 | 1.60 |
| 375 | 30 | 2:1 | 27.69 | 2.81 | 24.73 | 5.66 | 13.25 | 1.08 | 13.64 | 1.05 |
| 375 | 45 | 2:1 | 29.86 | 2.22 | 22.32 | 2.94 | 12.85 | 0.98 | 19.42 | 1.86 |
| 375 | 45 | 4:1 | 23.30 | 5.68 | 38.11 | 2.25 | 16.84 | 0.85 | 6.68 | 0.70 |
| 375 | 45 | 6:1 | 4.51 | 1.69 | 47.19 | 2.4 | 6.89 | 0.42 | 26.09 | 3.16 |

Example 12

Example 12 demonstrates the preparation of an unsupported copper/nickel catalyst.

115 g (0.48 mole) of $Cu(NO_3)_2 \cdot 4H_2O$ was dissolved in 250 ml of water. 145.5 g (0.5 mole) of $Ni(NO_3)_2 \cdot 6H_2O$ was dissolved in 250 ml $H_2O$ mixed together with the copper solution, and then added to 174 g (2.2 g) of $NH_4HCO_3$ dissolved in 2 L $H_2O$. The resulting slurry was stirred for 1 hr, allowed to settled overnight and filtered (paper filter). Solids were placed in a beaker with 2 L of water, stirred and filtered again. The mixed carbonates were dried in vacuum at 90° C. for 24 hrs. Then, they were crushed and calcined in air at 400° C. for 2 hrs, then, recrushed, placed into furnace and reduced in a regime as follows. The temperature was ramped from room temperature to 260° C. in He, The concentration of $H_2$ was increased to pure $H_2$ over 4 hrs, after which the temperature was increased to 350° C. and reduction was carried out for 16 hrs. The samples were passivated by cooling to room temperature in flowing He, gradually increasing the concentration of $O_2$ in the He stream over 2 hrs. 46 g of black powder was made. The powder was pressed and pelletized into 12-20 mesh size.

Example 13

Example 13 illustrates the conversion of CFC-1316mxx to HFC-1336mzz over the catalyst of example 12.

A Hastelloy reactor 15"L×1" o.d.×0.074" wall was filled with 10 cc (25 g) of Cu/Ni catalyst. The catalyst was conditioned at 50 sccm ($8.3 \times 10^{-7}$ m³/sec) hydrogen flow at 350° C. The hydrodechlorination of 1316mxx was studied at a temperature range of 250-325° C. and the products indicated in Table, below. Contact time was 15-60 seconds. The ratio of hydrogen to 1316mxx was 5:1 or 7:1. Products of the reaction were analyzed by GCMS to give the molar concentrations as listed in Table 12.

TABLE 12

| H2/1316 ratio | Contact Time, sec | Temp ° C. | t-1336 | 1345 | 356mff | c-1336 | t-1326mxz | t-1316mxx | c-1316mxx |
|---|---|---|---|---|---|---|---|---|---|
| 5:1 | 30 | 250 | 0.09 | 0.47 | 0.15 | 5.7 | 1.4 | 54.75 | 35.98 |
| 5:1 | 30 | 300 | 0.54 | 1.28 | 0.49 | 21.56 | 3.41 | 44.24 | 24.98 |
| 5:1 | 30 | 325 | 1.04 | 2.13 | 2.13 | 33 | 4.04 | 36.39 | 17.41 |
| 7:1 | 30 | 325 | 1 | 2.23 | 0.65 | 39.2 | 3.18 | 32.46 | 17.36 |
| 5:1 | 45 | 325 | 0.88 | 1.54 | 0.51 | 34.28 | 3.66 | 35.2 | 20.39 |
| 5:1 | 60 | 325 | 1 | 1.96 | 062 | 42.78 | 4.46 | 30.27 | 15.24 |
| 5:1 | 15 | 325 | 0.5 | 0.8 | 0.27 | 24.26 | 1.41 | 43 | 28.14 |

Example 14

Example 14 illustrates the conversion of 4,5-dichloroperfluoro-4-octene (CFC-171-14mccx) to 4,5-dihydroperfluoro-4-octene (173-14mccz) over Cu:Ni:Cr (0.5:0.48:0.02) catalyst.

An Inconel® tube (⅝ inch OD) was filled with 11 cc of Cu:Ni:Cr catalyst (12-20 mesh). The catalyst was activated at 350° C. for 2 hours under $H_2$ flow. 4,5-Dichloroperfluoro-4-octene was evaporated at 200° C., and fed to the reactor at a flow rate of 1 mL/hour. The reaction was run at 300° C. Table 13 below shows contact time and hydrogen to 171-14 ratio, and the composition of the reactor effluent as analyzed by GCMS to provide the following molar percent of products.

TABLE 13

| Temp ° C. | Contact time (sec) | Molar ratio $H_2$:171-14 | c-173-14 | t-172-14 | c-172-14 | t-171-14 |
|---|---|---|---|---|---|---|
| 300 | 30 | 10:1 | 53.1 | 5.2 | 7.7 | 22.6 |

Example 15

In a 400 ml Teflon beaker, a solution of 3.33 g $PdCl_2$ (60% Pd) in 100 ml 10% $HCl/H_2O$ was made. 98 g of $CaF_2$ was added to the beaker. The slurry was allowed to stand at RT for 1 Hr with occasional stirring and then dried at 110° C. with occasional stirring. The dried solid was crushed to a powder and the powder was reduced at 300° C. in a He—$H_2$ flow for 8 hrs. The initial gas composition forth reduction is 10% $H_2$, increasing to 100% over 4 hours. Then 2.45 g of lead acetate was dissolved in 100 ml of water. To the beaker with the lead acetate solution 99.3 g of 2% Pd/$CaF_2$ was added. The slurry was stirred at 50° C. for 2 hrs. The solid was collected on filter paper and dried at 110° C. for 16 hrs. The catalyst was pressed and pelletized to 12-20 mesh size.

Example 16

A Hastelloy reactor 15"L×1" o.d.×0.074" wall was filled with 5 cc of the catalyst of Example 15. The catalyst was conditioned at 50 sccm (8.3×10⁻⁷ m³/sec) hydrogen flow at 250° C. The hydrodechlorination of 1316mxx was studied over a temperature range of 200-300° C. and the products indicated in Table 14, below. Contact time was from 2.5 to 30 seconds. The ratio of hydrogen to 1316mxx was from 2:1 to 6.3:1 as indicated. Products of the reaction were analyzed by GCMS to give the molar concentrations as listed in Table 14.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below.

Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, any reference to values stated in ranges includes each and every value within that range.

What is claimed is:

1. A process for the preparation of fluorine-containing olefins comprising contacting a chlorofluoroalkene having the formula $R_fCCl$=$CClR_f$ wherein each $R_f$ is a perfluoroalkyl group independently selected from the group consisting of $CF_3$, $C_2F_5$, n-$C_3F_7$, i-$C_3F_7$, n-$C_4F_9$, i-$C_4F_9$ and t-$C_4F_9$, and wherein one of the $R_f$ groups may be F with hydrogen in the presence of a catalyst at a temperature sufficient to cause

TABLE 14

| H2/1316 ratio | Contact Time, sec | Temp ° C. | t-1336 | 356mff | c-1336 | t-1326mxz | 346mdf | t-1316mxx | c-1316mxx |
|---|---|---|---|---|---|---|---|---|---|
| 2:1 | 30 | 200 | 4.78 | 9.26 | 13.22 | 11.46 | 2.32 | 37.35 | 16.17 |
| 2:1 | 30 | 250 | 14.96 | 16.21 | 17.97 | 25.4 | 3.21 | 17.22 | 2.65 |
| 2:1 | 4 | 250 | 2.66 | 2.85 | 13.03 | 8.91 | 1.14 | 41.28 | 23.37 |
| 4:1 | 2.5 | 250 | 2.79 | 3.59 | 13.52 | 8.96 | 1.42 | 40.54 | 22.56 |
| 6.3:1 | 2.5 | 200 | 2.92 | 5.65 | 12.57 | 12.83 | 1.73 | 47.16 | 13.65 |
| 6.3:1 | 2.5 | 250 | 6.68 | 8.11 | 23.58 | 21.26 | 1.32 | 31.64 | 5.39 | replacement of the chlorine substituents of the chlorofluoroalkene with hydrogen to produce a fluorine-containing olefin having the formula E- or Z—$R^1$CH=CH$R^2$, wherein each of $R^1$ and $R^2$ are, perfluoroalkyl groups independently selected from the group consisting of $CF_3$, $C_2F_5$, n-$C_3F_7$, i-$C_3F_7$, n-$C_4F_9$, i-$C_4F_9$ and t-$C_4F_9$, and wherein $R^2$ may be F.

2. The process of claim 1 wherein said catalyst is selected from the group consisting of copper on carbon, copper on calcium fluoride, palladium on barium sulfate, palladium/barium chloride on alumina, Lindlar catalyst (palladium on $CaCO_3$, poisoned with lead), palladium on calcium fluoride poisoned with lead, copper and nickel on carbon, nickel on carbon, nickel on calcium fluoride, copper/nickel/chromium on calcium fluoride and unsupported alloys of copper and nickel.

3. The process of claim 1 wherein the said catalyst is selected from the group consisting of copper on carbon, copper on calcium fluoride, copper and nickel on carbon, nickel on carbon, copper/nickel/chromium on calcium fluoride and unsupported alloys of copper and nickel.

4. The process of claim 1 wherein each $R_f$ is $CF_3$.

5. The process of claim 1 wherein each $R_f$ is n-$C_3F_7$.

6. The process of claim 1 wherein each of $R^1$ and $R^2$ is $CF_3$.

7. The process of claim 1 wherein each of $R^1$ and $R^2$ is n-$C_3F_7$.

8. The process of claim 1 wherein the process is conducted at a temperature of from about 200° C. to about 450° C.

9. The process of claim 1 wherein the ratio of hydrogen to chlorofluoroalkene is from about 1:1 to about 10:1.

10. The process of claim 1 wherein the ratio of hydrogen to chlorofluoroalkene is from about 1:1 to about 7.5:1.

11. The process of claim 3 wherein the molar ratio of copper:nickel:chromium in the copper/nickel/chromium on calcium fluoride catalyst is about 0 to about 1 copper:about 0.5 to about 3.0 nickel, and about 0 to about 2 chromium.

12. The process of claim 3 wherein the amount of copper on carbon or calcium fluoride is from about 1% to about 25% by weight.

13. The process of claim 3 wherein the amount of copper on carbon or calcium fluoride is from about 5% to about 25% by weight.

* * * * *